US006370213B1

(12) United States Patent
Kim et al.

(10) Patent No.: US 6,370,213 B1
(45) Date of Patent: Apr. 9, 2002

(54) BANDED ECP SENSOR

(75) Inventors: Young Jin Kim, Clifton Park; Eric Moran, Schenectady, both of NY (US); Donald Allan Hale, San Jose, CA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/397,840

(22) Filed: Sep. 17, 1999

(51) Int. Cl.[7] ................................................ G21C 9/00
(52) U.S. Cl. ........................ 376/305; 376/245; 324/446; 324/724; 324/700; 324/72.5; 205/775; 205/794.5; 204/1; 204/400; 204/435; 73/61.41; 73/61.42; 73/763; 73/781
(58) Field of Search ................................ 376/305, 245; 204/1, 400, 435; 205/775, 794.5; 324/446, 724, 700, 72.5; 73/61.41, 61.42, 763, 781

(56) References Cited

U.S. PATENT DOCUMENTS

| 5,217,596 A | * | 6/1993 | Indig et al. ................. 204/435 |
| 5,465,281 A | | 11/1995 | Andresen et al. ........... 376/305 |
| 5,571,394 A | * | 11/1996 | Hettiarachchi et al. ..... 204/400 |
| 5,581,588 A | * | 12/1996 | Andresen .................... 376/305 |
| 5,719,911 A | * | 2/1998 | Hettiarachichi et al. .... 376/245 |
| 5,770,273 A | * | 6/1998 | Offer et al. ................. 427/455 |
| 5,793,830 A | * | 8/1998 | Kim et al. ................... 376/305 |
| 5,848,113 A | * | 12/1998 | Kim et al. ................... 376/305 |
| 5,896,432 A | * | 4/1999 | Kim et al. |
| 6,024,805 A | * | 2/2000 | Kim et al. ................... 148/240 |
| 6,181,760 B1 | * | 1/2001 | JinKim ........................ 376/245 |
| 6,222,307 B1 | * | 4/2001 | Roy et al. .................... 313/326 |

FOREIGN PATENT DOCUMENTS

| JP | 11-142363 | * | 6/1999 | ........... G21C/17/00 |
| JP | 11-148909 | * | 6/1999 | ........... G21C/17/02 |

OTHER PUBLICATIONS

Indig, "Electrochemical Sensors for Application to Boiling Water Reactors", Internatnional Corrosion Congress, Energy Science and Technology (DOE), 12th: 1993, pp. 4224–4236.

* cited by examiner

Primary Examiner—Michael J. Carone
Assistant Examiner—John Richardson
(74) Attorney, Agent, or Firm—Robert P. Santandrea; Noreen C. Johnson

(57) ABSTRACT

An ECP sensor includes a tubular ceramic probe having a closed tip at one end packed with a metal and metal oxide powder. A metal support tube receives an opposite end of the probe, and is joined thereto by a braze joint therewith. An electrical conductor extends through the support tube and probe, and has an end buried in the powder for electrical contact therewith. A ceramic band bridges the probe and tube at the joint for sealing thereof.

11 Claims, 2 Drawing Sheets

BANDED ECP SENSOR

BACKGROUND OF THE INVENTION

The present invention relates generally to nuclear reactors, and, more specifically, to electrochemical corrosion potential (ECP) sensors therein.

In a boiling water nuclear reactor, water and steam are channeled through various conduits formed of stainless steel. Normal water chemistry conditions include high oxidizing species, such as oxygen and hydrogen peroxide which may lead to intergranular stress corrosion cracking (IGSCC) of the stainless steel.

IGSCC can be mitigated by lowering the concentrations of ionic impurities and oxidizing species in the reactor water. This may be effected using hydrogen water chemistry (HWC) in which hydrogen is added to the feed water of the reactor. The primary purpose of the added hydrogen is to reduce the dissolved oxidant concentrations and thereby lower the ECP below a critical value at which IGSCC susceptibility is significantly reduced.

Various forms of ECP sensors are used for measuring ECPs in the reactor. The sensors have different configurations for measuring ECPs, and are subject to different problems which affect their useful lives. The useful life should cover the duration of at least a single fuel cycle which is about eighteen months in the United States. However, experience in actual nuclear reactors has demonstrated sensor failure in a shorter duration due to various causes.

U.S. Pat. Nos. 5,848,113 and 5,896,432, commonly owned by the present assignee, disclose and claim two different types of ECP sensors specifically configured for solving corresponding failure problems during operation.

A different type of ECP sensor includes a ceramic probe in which is packed a mixture of metal and metal oxide powder for providing a corresponding reference ECP. This mixture may include iron and iron oxide ($Fe/Fe_3O_4$), or copper and copper oxide ($Cu/Cu_2O$), or nickel and nickel oxide (Ni/NiO).

In this type of sensor, the probe is typically in the form of a zirconia tube brazed to a support tube made of a suitable metal such as Invar or "alloy 42", which in turn is welded to a stainless steel tube. An electrical conductor extends through the tubes into the probe and is buried in the operative mixture.

In one example, the ceramic probe is formed of magnesia-stabilized-zirconia (MSZ) brazed to an alloy 42 support tube. Since the ceramic probe and metal tube have different coefficients of thermal expansion, they are subject to thermal shock during high temperature operation inside the nuclear reactor which can lead to cracking of the braze joint. The braze material is also subject to corrosion during operation. Both problems limit the useful life of the sensor, since failure of the braze joint causes water leakage inside the sensor and failure thereof.

Accordingly, it is desired to provide an improved ECP sensor addressing these problems.

BRIEF SUMMARY OF THE INVENTION

An ECP sensor includes a tubular ceramic probe having a closed tip at one end packed with a metal and metal oxide powder. A metal support tube receives an opposite end of the probe, and is joined thereto by a braze joint therewith. An electrical conductor extends through the support tube and probe, and has an end buried in the powder for electrical contact therewith. A ceramic band bridges the probe and tube at the joint for sealing thereof.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
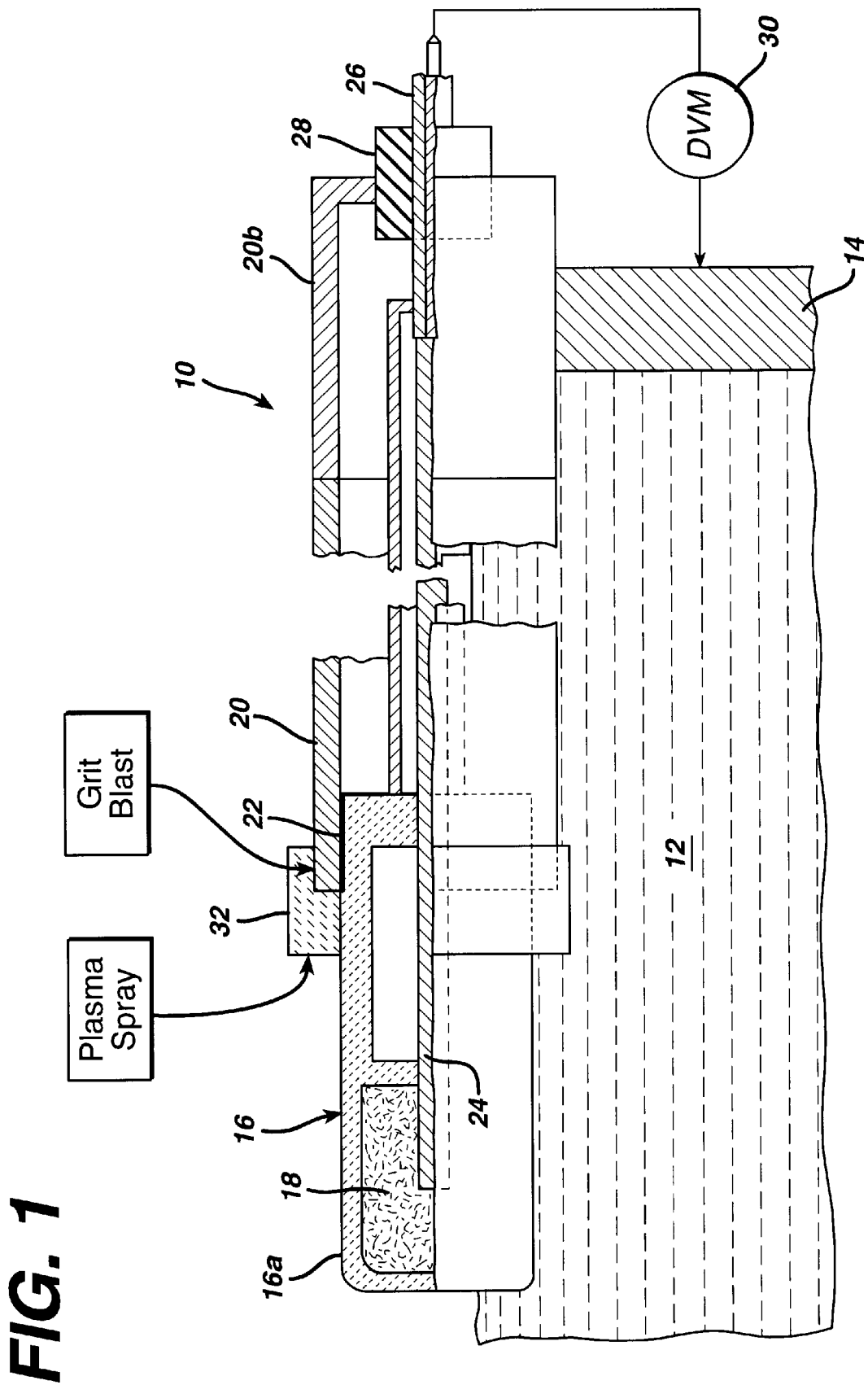
FIG. 1 is a schematic representation of an ECP sensor shown in relevant portion of a nuclear reactor in accordance with an exemplary embodiment of the present invention.

Illustrated schematically in FIG. 1 is an ECP sensor 10 configured for measuring electrochemical corrosion potential of reactor surfaces in circulating water 12 inside the pressure vessel of a conventional boiling water nuclear reactor 14, shown in relevant part.

The sensor includes a tubular ceramic probe 16 having a closed tip 16a in the form of a cup at a distal end of the probe packed with a dry metal and metal oxide mixture or powder 18.

A metal support tube 20 has a distal end receiving an opposite, proximal end of the probe for support thereof, and is joined thereto by a braze joint 22 therewith. The support tube 20 may be formed of conventional alloy 42 or Invar, for example. The braze joint may be a conventional alloy, such as silver, copper, and titanium alloy. The support tube 20 is typically welded coaxially with a secondary support tube 20b typically formed of stainless steel.

An electrical conductor 24 extends coaxially through the support tubes 20, 20b and the probe 16, and has a distal end buried in the powder 18 for electrical contact therewith. A coaxially electrical cable 26 extends through a suitable sealing collar 28 at the proximal of the secondary tube 20b and is suitably joined to the electrical conductor 24 inside the sensor. The cable 26 is suitably routed to a conventional digital volt meter 30 for measuring electrochemical corrosion potential.

The sensor 10 as above described is conventional in configuration and operation in the reactor. In one embodiment, the powder 18 is a mixture of iron and iron oxide ($Fe/Fe_3O_4$) for providing a constant reference potential of −820 mV vs standard hydrogen electrode (SHE) at 288° C. in high purity water.

As indicated above, this type of sensor is subject to thermal shock and corrosion at the braze joint 22 during operation, but for the improvement in accordance with the present invention. In a preferred embodiment, a ceramic band 32 is selectively applied around the perimeter of the sensor for bridging the probe and support tube at the braze joint for covering and sealing thereof.

The band 32 preferably locally coats the probe and support tube at the braze joint and is spaced from the remainder of the probe including its tip 16a.

The ceramic probe 16 may be formed of magnesia-stabilized-zirconia (MSZ) or yttria-stabilized-zirconia (YSZ) which have different coefficients of thermal expansion than that of the metal support tube 20, and that of the braze joint 22.

The ceramic band 32 is preferably also zirconia, such as MSZ or YSZ for matching the coefficient of thermal expansion of the ceramic probe. Since the band 32, like the probe 16, has a different coefficient of thermal expansion than that of the support tube 20 and braze joint 22, it is preferably applied locally or selectively solely at the exposed end of the braze joint 22 between the probe and support tube.

In one embodiment, the ceramic band 32 is directly bonded to the probe and tube at the braze joint in a coating effected using conventional plasma spraying equipment. The band 32 thusly provides an intimate bond with the probe and support tube for providing an effective seal at the juncture therebetween in which is found the braze joint 22.

A relatively thin coating of the ceramic band 32 of about 5–10 mils thick (0.13–0.25 mm) provides thermal shock and corrosion protection of the braze joint for extending the useful life of the sensor. The coating band may be applied using plasma spraying in vacuum or in air to produce a relatively high density coating of up to about 97% density. The thin and narrow band of ceramic coating accommodates differential thermal expansion and contraction between the probe and the support tube for reducing the likelihood of cracking thereat.

Figure 2:
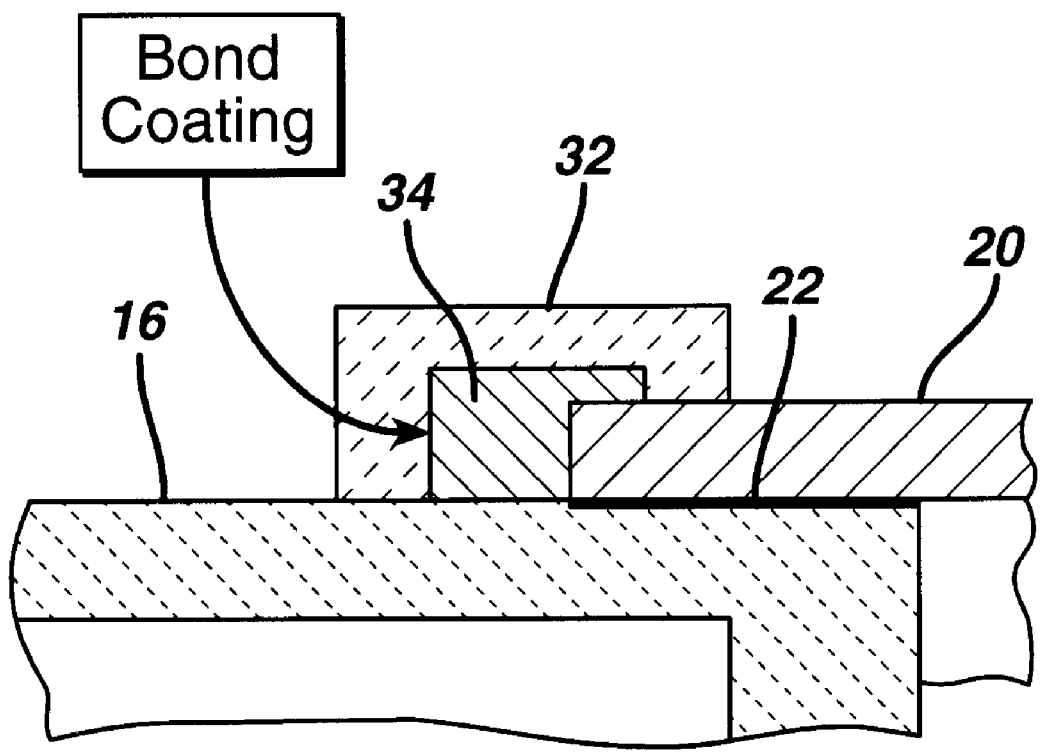
FIG. 2 is an enlarged, sectional view of a portion of the sensor illustrated in FIG. 1 in accordance with an alternate embodiment.

FIG. 2 illustrates an alternate embodiment of the sensor illustrated in FIG. 1 in which a bond coating 34 is firstly applied at the junction of the probe and support tube for enhancing the adherence of the ceramic band 32 atop the metal support tube 20. In either embodiment illustrated in FIGS. 1 and 2, the surfaces of the probe and support tube are prepared using conventional grit blasting, followed in turn by the bond coating 34, if used, and the ceramic band 32.

The bond coating 34 may be about the same thickness as that of the ceramic band 32 and is also locally applied in the immediate region of the junction between the probe and the support tube. The bond coating may be conventionally applied, such as by plasma spraying. And any suitable bond coating may be used, such as Nickel 210, which is a nickel-chrome-iron-aluminum alloy, or MCrAlY alloy, where M is nickel-cobalt-iron or nickel-cobalt alloy. The bond coating 34 underlays in most part the ceramic band for improving its adherence to at least the metal support tube.

In a preferred embodiment, the powder 18 is a mixture of iron and iron oxide trapped within a MSZ ceramic probe 16 brazed to an alloy 42 support tube 20. The ceramic band 32 is preferably YSZ.

In alternate embodiments, the powder 18 may be a mixture of copper and copper oxide ($Cu/Cu_2O$), or a mixture of nickel and nickel oxide (Ni/NiO), both in corresponding MSZ probes 16.

The ceramic band 32 thusly provides a hermetic water seal at the braze joint, and a thermal barrier providing thermal insulation. YSZ is the preferred material for the band 32 as having had proven resistance to high temperature and high flow water under high radiation environments in nuclear reactors.

The YSZ ceramic band 32 additionally provides electrical insulation for preventing the formation of a corrosion cell, even after long term exposure to high temperature water under various water chemistry conditions possible in a nuclear reactor environment. The YSZ ceramic coating therefore has proven stability for this hostile environment.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by letters patent of the united states is the invention as defined and differentiated in the following claims in which we claim:

What is claimed is:

1. A sensor for measuring electrochemical corrosion potential in a nuclear reactor comprising:

a tubular ceramic probe having a closed tip at one end packed with a metal and metal oxide powder;

a metal support tube having one end receiving an opposite end of said probe, and joined thereto by a braze joint therewith;

an electrical conductor extending through said support tube and probe, and having an end buried in said powder for electrical contact therewith; and a plasma sprayed ceramic band disposed on an outer surface of said tubular ceramic probe and said metal support tube, said plasma sprayed ceramic band bridging said tubular ceramic probe and said metal support tube at said joint for sealing thereof, said plasma sprayed ceramic band having a coefficient of expansion that is compatible with that of said tubular ceramic probe.

2. A sensor according to claim 1 wherein said band locally coats said probe and tube at said braze joint, and is spaced from said probe tip.

3. A sensor according to claim 2 wherein both said probe and band comprise zirconia.

4. A sensor according to claim 3 wherein said powder comprises iron and iron oxide.

5. A sensor according to claim 3 wherein said powder comprises copper and copper oxide.

6. A sensor according to claim 3 wherein said powder comprises nickel and nickel oxide.

7. A sensor according to claim 3 wherein said band comprises yttria-stabilized-zirconia or magnesia-stabilized-zirconia.

8. A sensor according to claim 3 wherein said band is directly bonded to said probe and tube at said braze joint.

9. A sensor according to claim 3 further comprising a bond coating underlaying said band and bonded to said probe and tube at said braze joint.

10. A sensor according to claim 3 wherein said probe comprises magnesia-stabilized-zirconia.

11. The sensor according to claim 1, further comprising a bond layer, said bond layer underlaying said band and being bonded to said probe and tube at said braze joint.

* * * * *